United States Patent [19]
Ogden et al.

[11] Patent Number: 5,662,101
[45] Date of Patent: Sep. 2, 1997

[54] RESPIRATORY FACIAL MASK

[75] Inventors: Douglas R. Ogden, Arvada, Colo.; Joseph A. Abeyta, Arlington, Tex.; Gregg D. Keefe, Boulder, Colo.

[73] Assignee: Respironics, Inc., Murrysville, Pa.

[21] Appl. No.: 568,961

[22] Filed: Dec. 7, 1995

[51] Int. Cl.$^6$ .................................... A62B 18/02
[52] U.S. Cl. .................... 128/205.25; 128/202.27; 128/206.24; 128/207.11; 128/912
[58] Field of Search .................. 128/202.27, 205.25, 128/206.24, 207.11, 912

[56] References Cited

U.S. PATENT DOCUMENTS

| | | | |
|---|---|---|---|
| 2,706,983 | 4/1955 | Matheson et al. | 128/146 |
| 2,837,090 | 6/1958 | Bloom et al. | 128/146 |
| 3,330,274 | 7/1967 | Bennett | 128/146.7 |
| 3,416,521 | 12/1968 | Hamlin | 128/146.7 |
| 3,824,999 | 7/1974 | King | 128/912 |
| 3,978,854 | 9/1976 | Mills, Jr. | 128/912 |
| 4,274,406 | 6/1981 | Bartholomew | 128/912 |
| 4,603,692 | 8/1986 | Montesi | 128/207.11 |
| 4,676,241 | 6/1987 | Webb et al. | 128/912 |
| 4,907,584 | 3/1990 | McGinnis | 128/206.24 |
| 4,960,121 | 10/1990 | Nelson et al. | 128/205.25 |
| 5,005,571 | 4/1991 | Dietz | 128/206.24 |
| 5,054,482 | 10/1991 | Bales | 128/912 |
| 5,074,297 | 12/1991 | Venegas | 128/204.18 |
| 5,243,971 | 9/1993 | Sullivan et al. | 128/205.25 |
| 5,265,595 | 11/1993 | Rudolph | 128/204.18 |
| 5,517,986 | 5/1996 | Starr et al. | 128/206.24 |
| 5,542,128 | 8/1996 | Lomas | 128/207.11 |
| 5,570,689 | 11/1996 | Starr et al. | 128/207.11 |

FOREIGN PATENT DOCUMENTS 8701950  4/1987  United Kingdom.

*Primary Examiner*—Aaron J. Lewis
*Attorney, Agent, or Firm*—W. Scott Carson

[57] ABSTRACT

A facial mask assembly for covering at least the nose and nares of a patient's face and compensating for any unequal forces that may be generated in the straps holding the mask on the patient's face. The assembly includes a rigid, cup-shaped shell with a soft seal engaging and sealing against the patient's face. The shell is preferably secured or attached to the patient's head by an arrangement including a rigid plate mounted to the rigid shell and a harness. The harness extends about the back of the patient's head and preferably has side straps attached to the top of the rigid plate. The rigid plate is loosely mounted to the rigid shell at at least three locations and can move to compensate for any unequally applied forces that would otherwise tend to rock or cock the shell off the patient's face and create a gap or leak in the seal. The invention also includes a modified hose coupling that permits the rigid shell and the flexible hose connected to the respiratory device to rotate relative to each other about multiple axes.

36 Claims, 8 Drawing Sheets

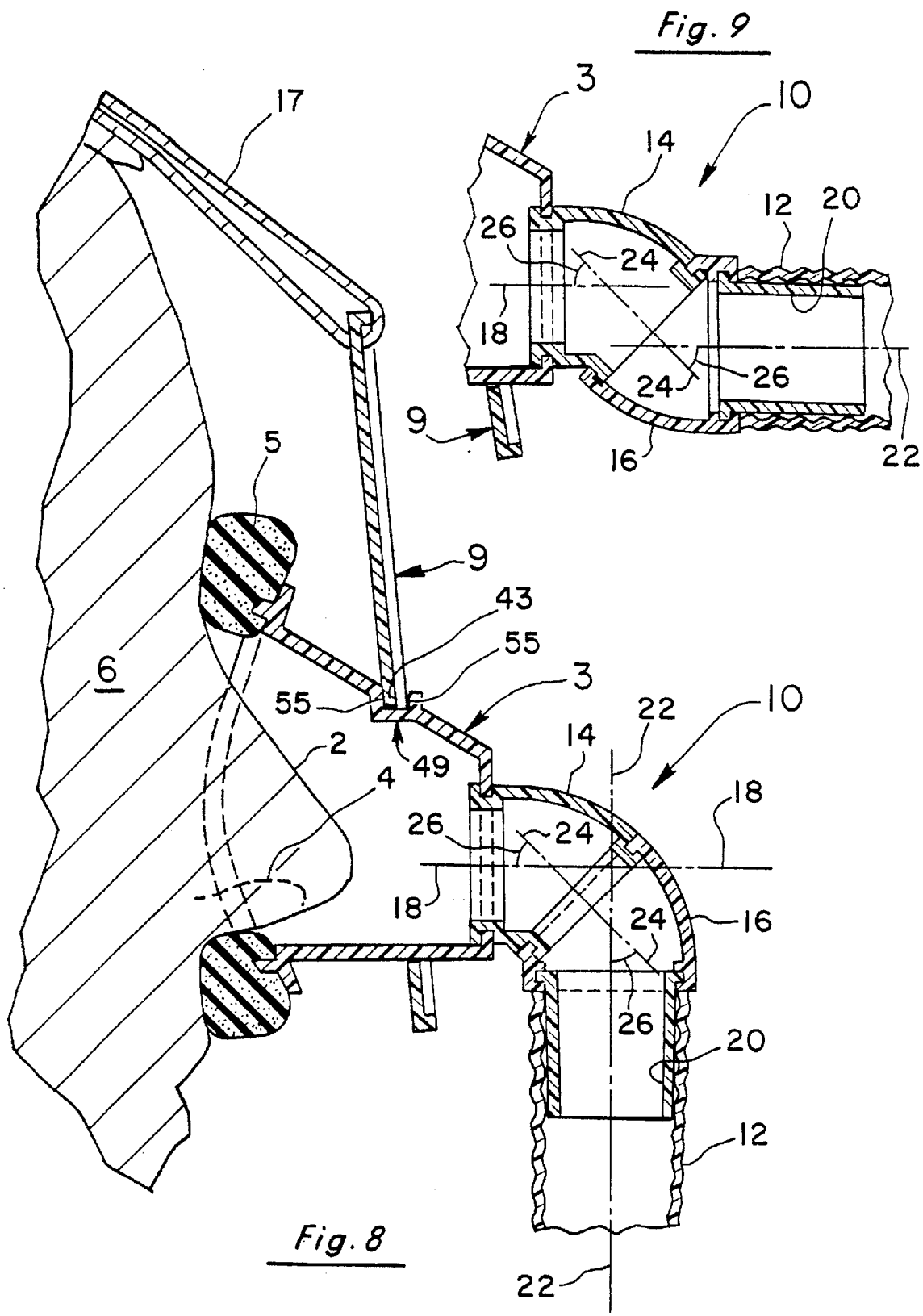

5,662,101

RESPIRATORY FACIAL MASK

BACKGROUND OF THE INVENTION

1. Field of the Invention.

This invention relates to the field of respiratory facial masks.

2. Discussion of the Background

Facial mask assemblies are widely used in respiratory care and therapy. Typically, the mask is sized to fit over the patient's nose (i.e., nasal mask) or nose and mouth (i.e., full face mask) and seal against the patient's face. The mask is commonly held in place by a harness arrangement that includes straps that extend about the back of the patient's head and are attached at multiple points (e.g., sides and top) to the mask itself. In use, a common problem often arises that the mask will tend to unseat and leak as the patient turns his or her head (e.g., from side-to-side) or rolls over in bed and the straps contact and are deflected by a pillow, blanket, or other object.

More specifically, as the patient for example moves his or her head from side-to-side, the skin and muscles of the head tend to move relative to the underlying skull bones. The end result is that the side straps pull with unequal forces on the mask (i.e., the side strap away from the direction of movement tends to draw tighter while the other side strap slackens). This can cause the mask to cock or rock off the patient's face creating a leak or gap between the mask and the side of the patient's face in the direction of movement. The same unequal forces and resulting leakage can be created if the patient rolls over and one of the straps contacts and is deflected laterally by a pillow, blanket, or other object. Various devices and modifications to mask structures have been developed to compensate for these undesirable effects; however, most of them are awkward and cumbersome and have not been widely accepted by patients and doctors.

With this in mind, the present invention was made. With it, a simple and effective way has been devised to compensate for the unequal forces that may develop on such facial masks and to prevent these unequal forces from unseating the mask and causing it to leak.

SUMMARY OF THE INVENTION

This invention relates to a facial mask assembly for covering at least the nose and nares of a patient's face and compensating for any unequal forces that may be generated in the straps holding the mask on the patient's face. The assembly includes a rigid, cup-shaped shell with a soft seal engaging and sealing against the patient's face. The shell is preferably secured or attached to the patient's head by an arrangement including a rigid plate mounted to the rigid shell and a harness. The harness extends about the back of the patient's head and preferably has side straps attached to the sides of the rigid plate and a top strap attached to the top of the rigid plate. The rigid plate is loosely mounted to the rigid shell at at least three locations. Consequently, in use, the rigid plate is free to move relative to the rigid shell in response to any unequal forces being applied to it by the side straps as the patient, for example, turns his or her head from side-to-side.

In this regard, the movement of the rigid plate compensates for any unequally applied forces that would otherwise tend to rock or cock the shell off the patient's face and create a gap or leak in the seal. In the preferred embodiment, this is accomplished by allowing or permitting the rigid plate to selectively rotate about axes through any two of the three locations at which the rigid plate is loosely mounted to the rigid shell. This essentially serves to decouple the sealing function of the rigid shell and its seal from the attaching function of the harness straps which secure the shell to the patient's head. The invention also includes a modified hose coupling that permits the rigid shell and the flexible hose connected to the respiratory device to rotate relative to each other about multiple axes. Taken together, the modified hose coupling and loosely mounted rigid plate can accommodate a wide variety of motions and forces while maintaining the sealed shell stationary on the patient's face. The patient, hose, and respiratory device can then move or be moved almost at will without breaking the seal of the mask.

BRIEF DESCRIPTION OF THE DRAWINGS

FIG. 8 is a view taken along line 8—8 of FIG. 7.

FIG. 9 in addition to FIG. 8 illustrates the modified hose coupling of the present invention which allows the rigid shell and flexible hose connected to the respiratory device to rotate relative to each other about multiple axes.

DETAILED DESCRIPTION OF THE PREFERRED EMBODIMENTS

Figure 1:
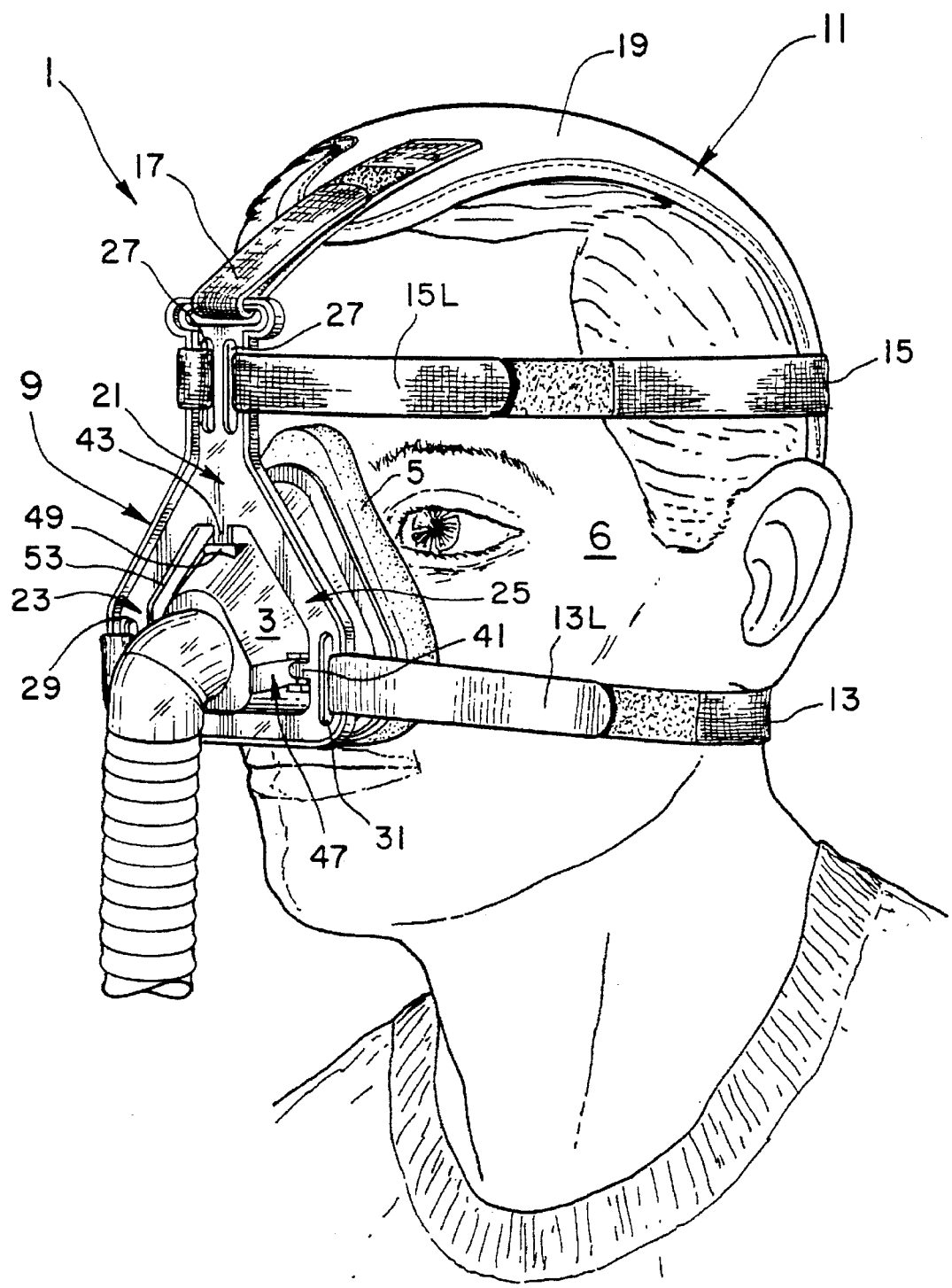
FIG. 1 is a perspective view of the facial mask assembly of the present invention positioned on the patient's face.
Figure 2:
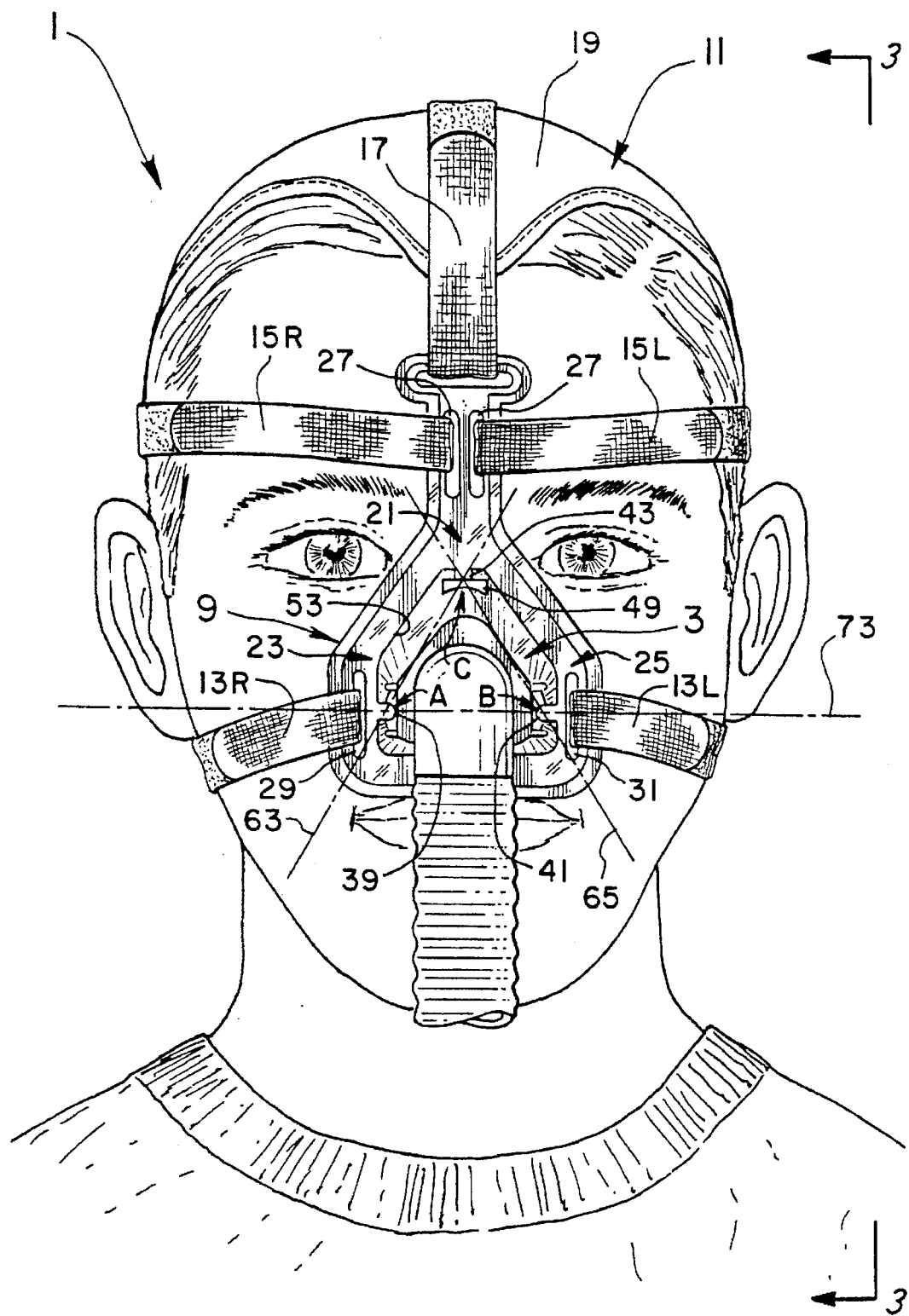
FIG. 2 is a front view of the mask in use taken along line 2—2 of FIG. 3.
Figure 3:
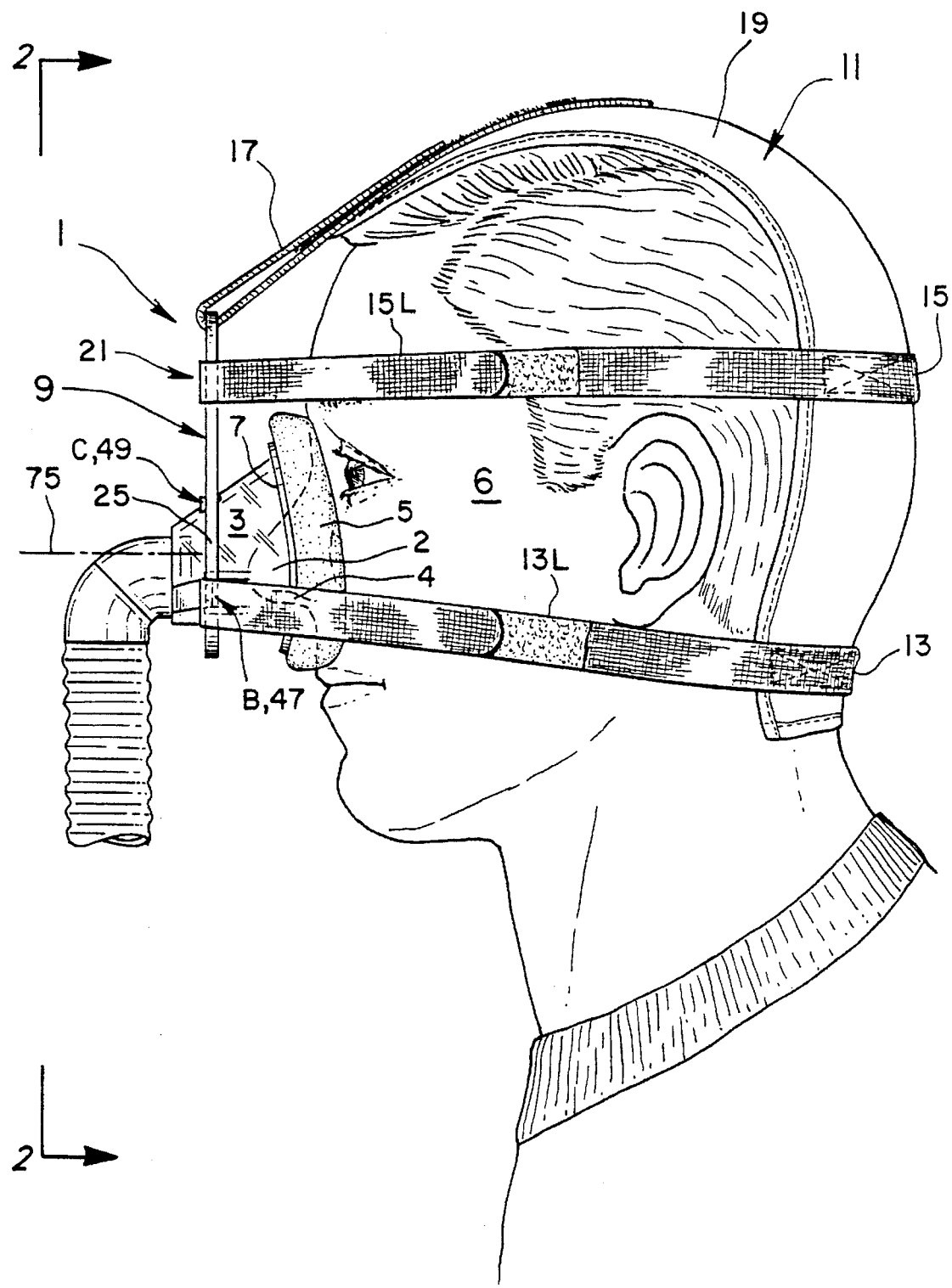
FIG. 3 is a side view thereof taken along line 3—3 of FIG. 2.

Referring to FIGS. 1–3, the facial mask assembly 1 of the present invention is illustrated as a nasal mask covering the nose 2 and nares 4 (see FIG. 3) of the patient 6 but the invention is equally applicable to full face masks covering the patient's nose and mouth. In the illustrated embodiment of a nasal mask, the facial mask assembly 1 of the present invention includes a rigid, cup-shaped shell 3 made of hard plastic and dimensioned to surround and enclose the patient's nose 2 and nares 4. A soft, pliable seal 5 of elastomer, urethane foam, or rubber is attached (e.g., glued or press fit) about the rear perimeter portion 7 of the rigid shell 3 to engage and seal against the patient's face. The rigid, cup-shaped shell 3 with its seal 5 (see FIGS. 1–3) is attached or secured in its sealing position enclosing the nose 2 and nares 4 of the patient 6 by the rigid plate 9 and harness arrangement 11.

The preferred harness arrangement 11 as illustrated is a five-point attachment one with lower side straps 13R and 13L which extend under the ears and about the back of the patient's head, upper side straps 15R and 15L, and top strap 17. The side straps 13R and 13L (R for right and L for left) can each be separate straps attached to the skull cap 19 like the top strap 17 or can be ends of a single strip 13. The same is true for side straps 15R and 15L. In the preferred embodiment, all five, flexible straps 13R, 13L, 15R, 15L, and 17 are used but at a minimum, at least the lower side straps 13R and 13L and top strap 17 (or the lower side straps 13R and 13L and the upper side straps 15R and 15L) are used. The upper side straps in this last regard could be the two straps 15R and 15L as illustrated or one continuous strap passing through loops 27 and anchoring the top portion 21 of the rigid plate 9 (see FIGS. 1–3). In any event, each side strap 13R and 13L is preferably attached to a respective side portion 23, 25 of the rigid plate 9 on respective sides of the patient's nose 2. This can be done in any number of well-known, adjustable manners including looping the straps 13R and 13L through the openings 29, 31 in the rigid plate 9 and fastening them back on themselves by hook and loop materials on the straps themselves. Snaps and similar arrangements could also be used if desired. The remaining straps 15R, 15L, and 17 are also individually attachable in this manner although the straps 15R and 15L could be one continuous strip through the loops 27 if desired as discussed above. The straps themselves are preferably made of flexible material and may have some slight elasticity to them to comfortably fit about the patient's head.

The rigid plate 9 as illustrated in FIGS. 1–3 is preferably flat or planar and made of relatively hard plastic. The rigid plate 9 as best seen in FIGS. 2 and 3 is mounted to the rigid shell 3 at at least three locations A, B, and C by detents 39, 41, and 43 respectively received in channels 45, 47, and 49 (see also FIGS. 1, 6, and 7). Channels 45 and 47 are located on each side of the rigid shell 3 and loosely receive the substantially mating detents 39 and 41 located on the side portions 23, 25 of the rigid plate 9 (see again FIGS. 1–3 and 6–7). Additionally, the third channel 49 is located along the top rigid portion of the shell 3 which extends along and over the ridge of the patient's nose 2. The channel 49 loosely receives the substantially mating detent 43 therein. The detents 39, 41, and 43 as seen in FIGS. 1 and 2 extend inwardly of the aperture 53 in the rigid plate 9. The aperture 53 is dimensioned to receive at least part of the top ridge portion and front of the rigid shell 3 and can extend completely or only partially about the shell 3.

Figure 6:
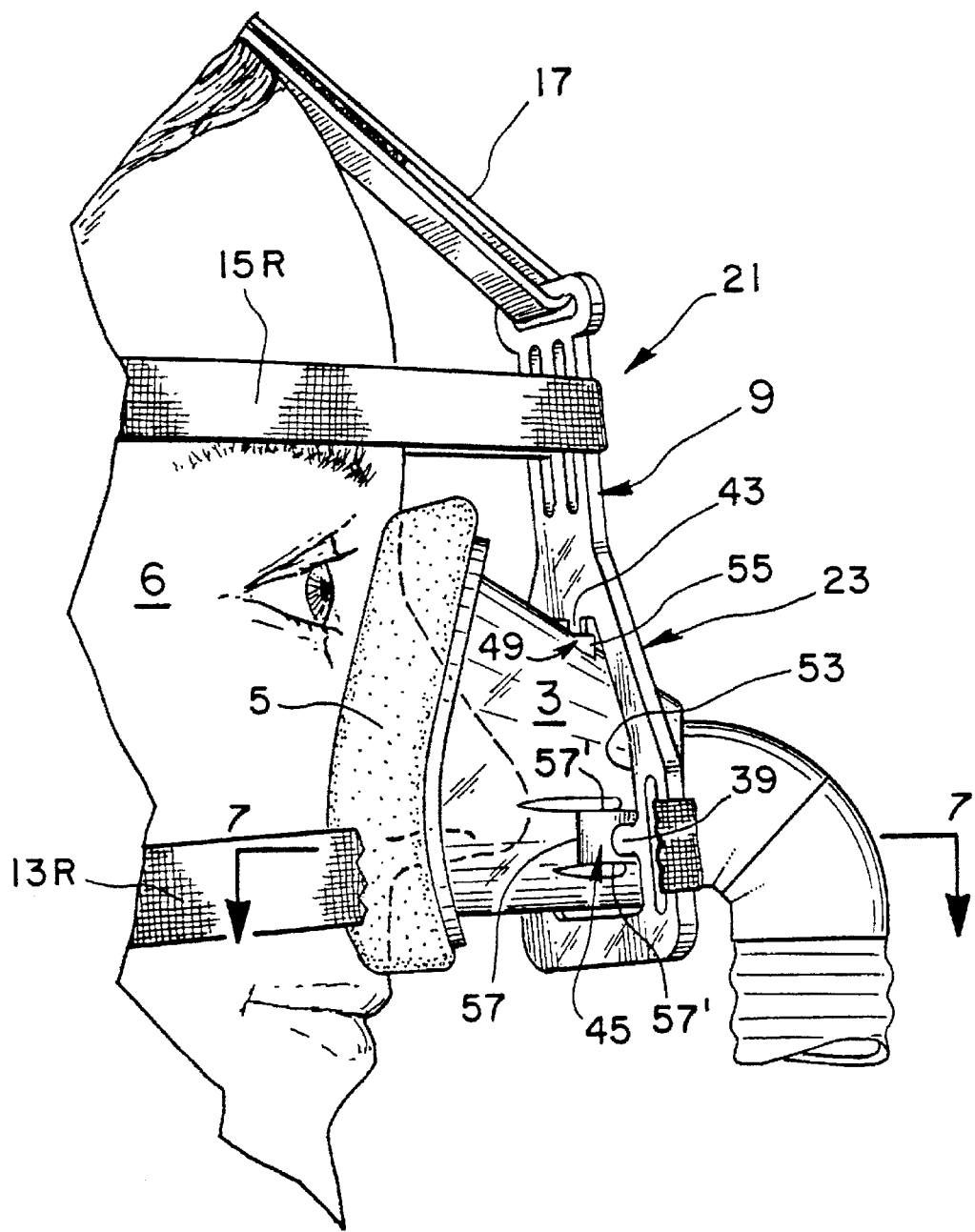
FIG. 6 is a view taken along line 6—6 of FIGS. 5 and 7 with the side strap partially broken away for clarity.
Figure 7:
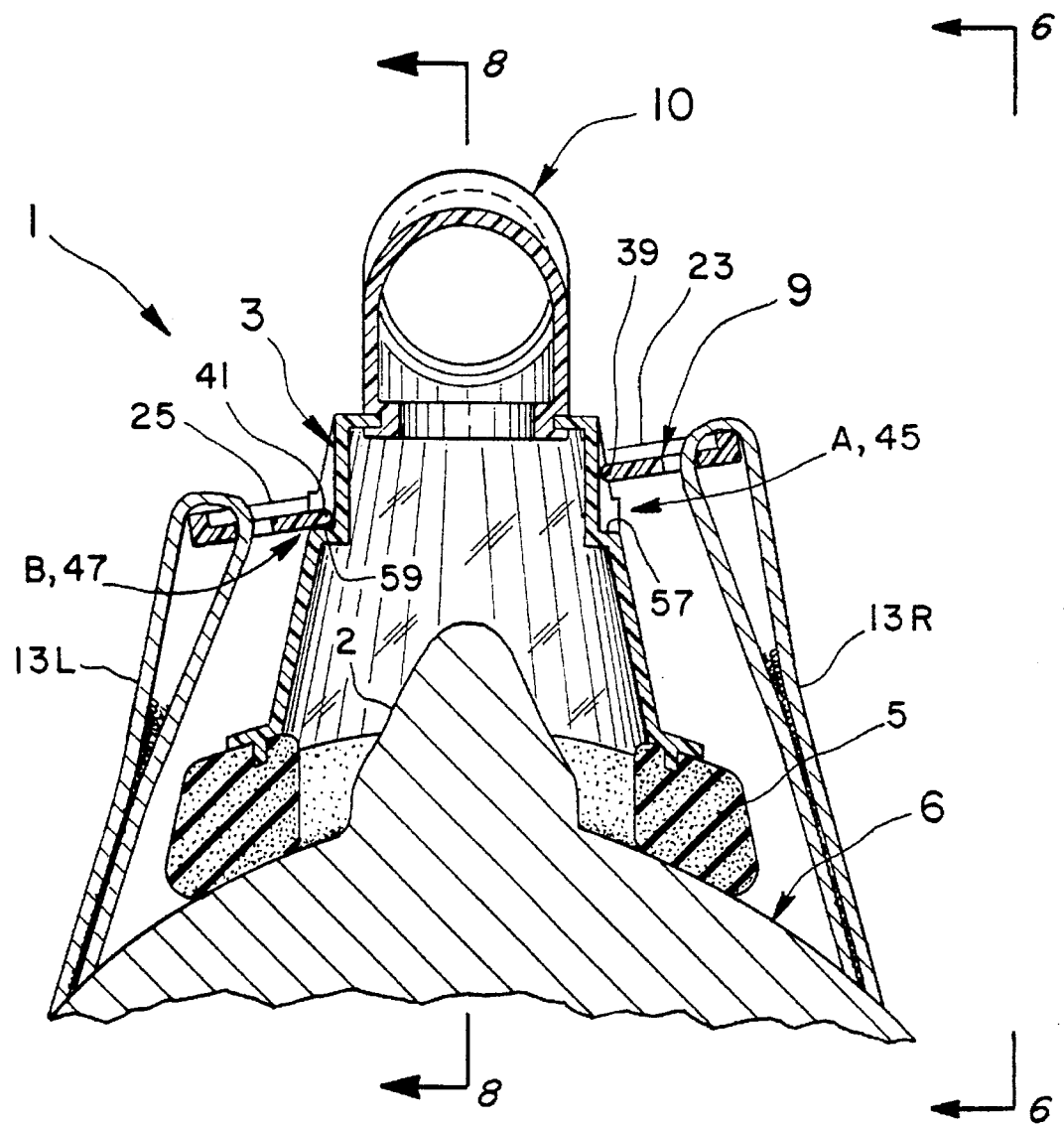
FIG. 7 is a view taken along line 7—7 of FIG. 6 and rotated ninety degrss for clarity.

The top channel 49 is different from the side channels 45 and 47 in that the top channel 49 preferably captures and maintains the third detent 43 within the four end walls 55 of the channel 49 (see FIGS. 6 and 8). In contrast, each side channel 45 and 47 (as best seen in FIGS. 6 and 7) has a closed, rear end at respective walls 57 and 59 but is open ended at the front. The rigid plate 9 is then free to selectively rotate relative to the rigid shell 3 about the axes 63 and 65 of FIG. 2. In this manner as explained in more detail below, the rigid plate 9 can selectively rotate about these axes 63 and 65 to compensate for any unequal forces applied to the rigid plate 9, as for example, by side straps 13R and 13L as the patient turns his or her head from side-to-side.

Figure 4:
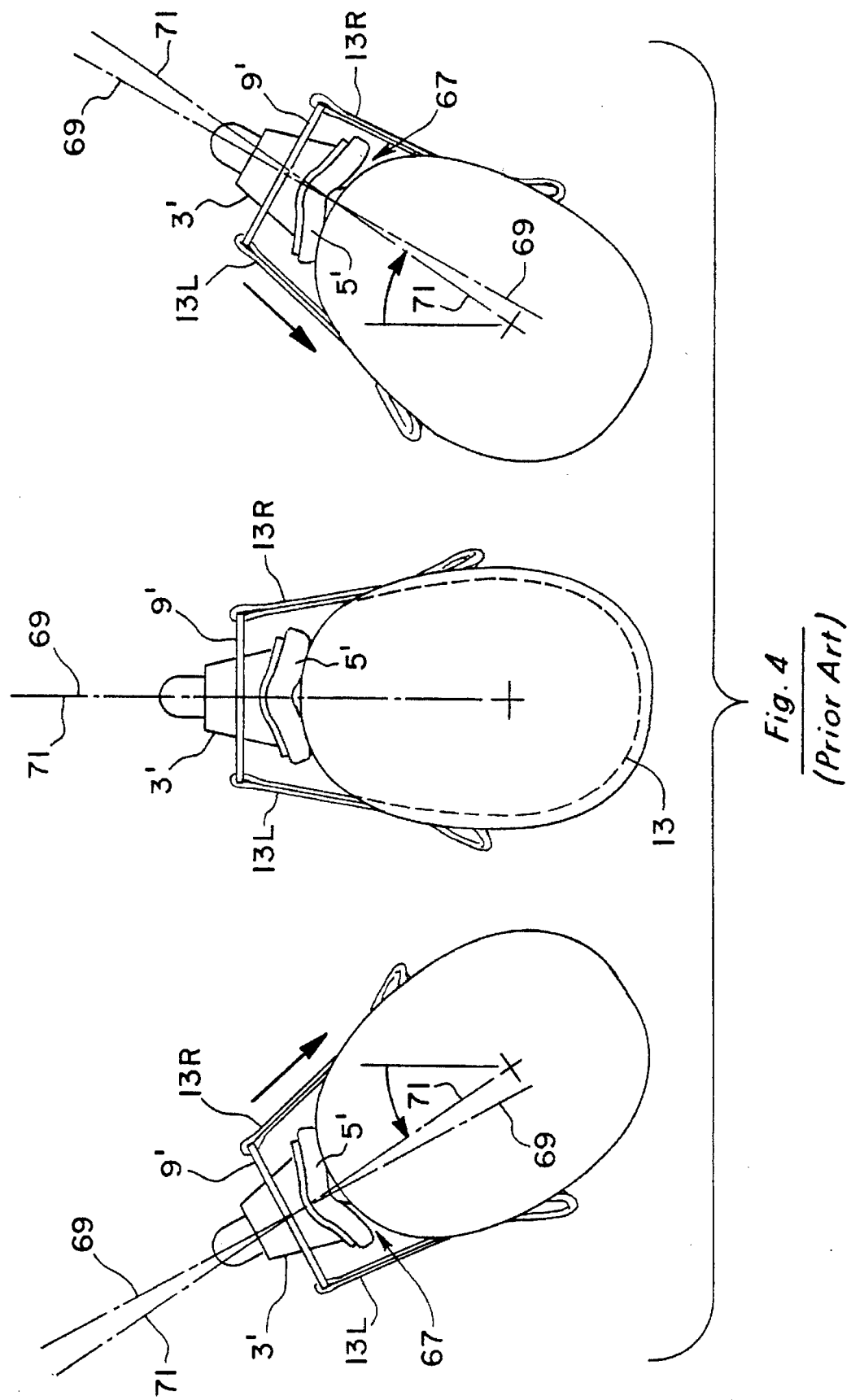
FIG. 4 is an overhead, schematic view of a prior mask assembly illustrating the manner in which the mask will tend to rock or cock and unseat itself as the patient turns his or her head from side-to-side.

More specifically and referring to the prior art arrangement of FIG. 4, previous mask assemblies of similar construction to the present invention fixedly mounted the rigid plate 9' to their shell 3'. Consequently as shown in FIG. 4, when the patient turned his or her head to either side, the side strap 13R or 13L away from the direction of motion would have a tendency to tighten or pull harder on the rigid plate 9'. This in turn would tend to lift the rigid shell 3' and its seal 5' off the side of the patient's face breaking the seal. As explained above, side straps 13R and 13L are essentially the ends of a single strap 13 preferably attached to the skull cap 19 and extending about the back of the patient's head. The mask lifting is then primarily a result of this taut strap 13 about the back of the patient's head moving with the skin and muscles of the patient relative to the underlying skull bones as the patient turns from side-to-side. For example and referring to FIG. 4, when the patient turns his or her head from the central position of FIG. 4 to the left, the right side strap 13R is drawn tighter or harder than the left side strap 13L. This tends to lift the left side of the shell 3' and its seal 5' off the patient's face creating a leak or gap at 67. In effect, this prior art approach causes the center line 69 of the shell 3' to become misaligned with the center line 71 of the patient's head and face.

Figure 5:
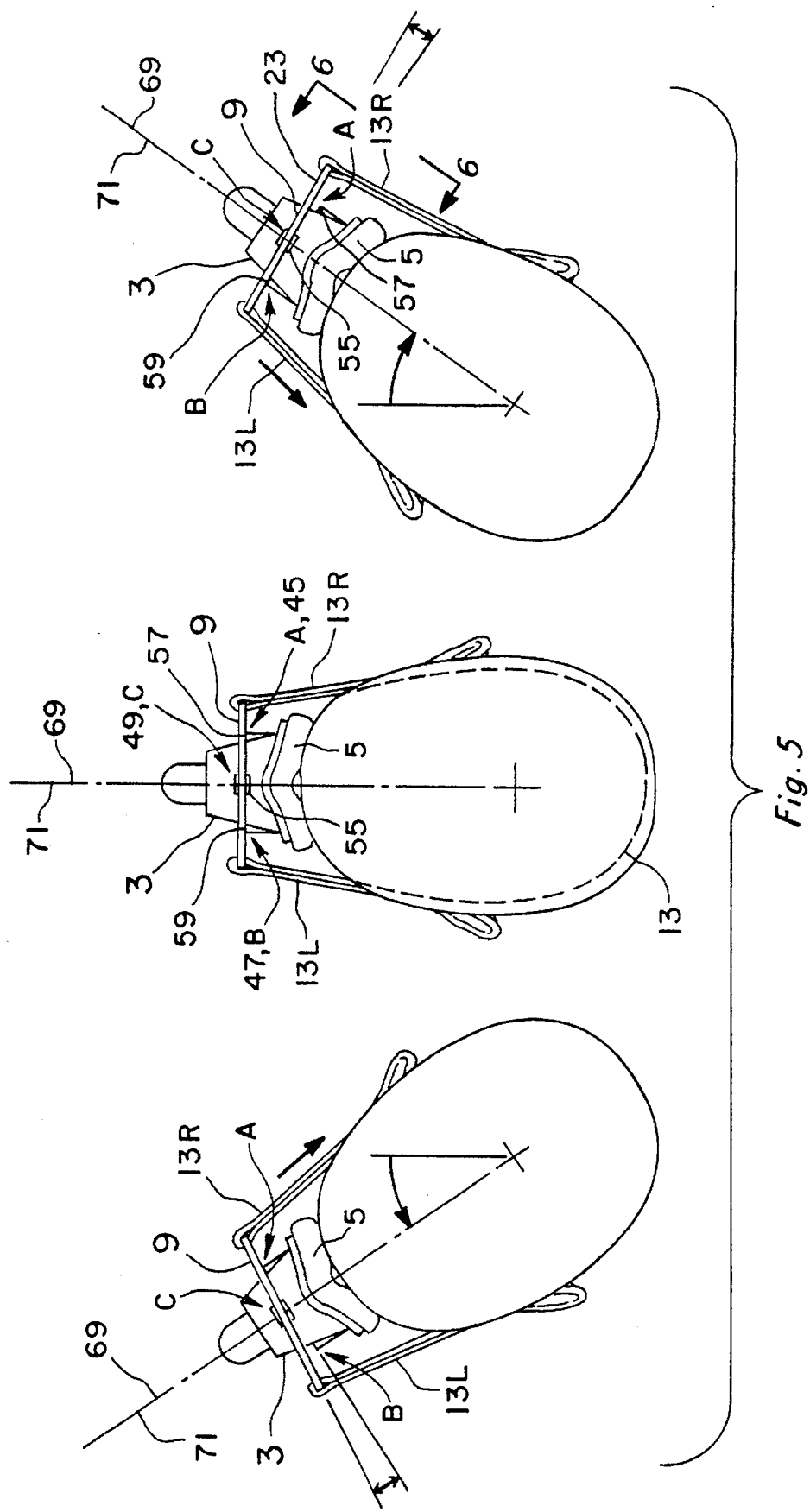
FIG. 5 is a view similar to FIG. 4 but illustrating the manner in which the facial mask assembly of the present invention will rotate the rigid plate relative to the rigid shell to compensate for any unequally applied forces tending to unseat the mask as the patient turns his or her head from side-to-side.

In contrast and referring to FIG. 5, the facial mask assembly 1 of the present invention loosely mounts the rigid plate 9 to the rigid shell 3 so the rigid plate 9 can rotate relative to the rigid shell 3 when the forces applied to side straps 13R and 13L are unequal. In essence, the rigid plate 9 is permitted or allowed to rotate to compensate for any unequally applied forces as the patient moves his or her head. As mentioned above, this is largely accomplished by mounting the rigid plate 9 to the rigid shell 3 at the three locations A, B, and C by the loosely mating detent-channel pairs 39/45, 41/47, and 43/49. In this manner and with the shell 3 of the facial mask assembly 1 centered on the patient's face and the patient looking straight ahead (central position of FIG. 5), the patient can adjust the side straps 13R and 13L to comfortably apply equal forces to the rigid plate 9. All of the detents 39, 41, and 43 on the rigid plate 9 are then pulled back in this position to abut the respective end or rear walls 55, 57, and 59 of the three channels 45, 47, and 49. However, when the patient turns his or her head and instead of tending to lift the shell 3 and its seal 5 off the patient's face and breaking the seal as in FIG. 4, the rigid plate 9 of the present invention in FIG. 5 rotates relative to the rigid shell 3. This movement then compensates or equalizes the forces and keeps the shell 3 securingly in place with the center lines 69 and 71 of the shell 3 and the patient's face aligned.

The actual movement of the rigid plate 9 relative to the rigid shell 3 is preferably about either of the axes 63 and 65 in FIG. 2. That is, in the central position of FIGS. 2 and 5, the detents 39, 41, and 43 are respectively abutting the back or rear end walls 55, 57, and 59 of the channels 45, 47, and 49. However, as the patient for example turns his or her head to the right in FIG. 5 and the forces applied by side straps 13L and 13R become unequal (i.e., the force on strap 13L becomes greater than the force on strap 13R), the rigid plate 9 actually rotates about the axis 65 (see FIG. 2) extending through the detent-channel locations at B and C. The right side portion 23 and detent 39 of rigid plate 9 then move away from the back wall 57 of channel 45 and along the channel side walls 57' (see FIGS. 5 and 6). Conversely, as the patient turns his or her head to the left in FIG. 5 and the forces applied by side strap 13R becomes greater than the force applied by side strap 13L, the rigid plate 9 rotates about the axis 63 (see FIG. 2) extending through locations A and C. The left side portion 25 and detent 41 of rigid plate 9 then move away from the back wall 59 of channel 47.

Stated another way, the rigid plate 9 is preferably mounted to the rigid shell 3 at first, second, and third locations A, B, and C. As the patient turns his or her head to the left in FIG. 5 and the force on side strap 13R becomes greater than on side strap 13L, the rigid plate 9 rotates about the first axis 63 that extends substantially through the first and third locations A and C of FIG. 2. Similarly, if the patient turns to the right in FIG. 5, the rigid plate 9 will rotate about the second axis 65 of FIG. 2 that extends substantially through the second and third locations B and C. In this manner, the facial mask assembly 1 is able to compensate for any unequally applied forces by the side straps 13R and 13L.

In effect, the facial mask assembly 1 of the present invention with its force compensating feature decouples or isolates the sealing function of shell 3 and its seal 5 from the attaching function of the harness straps that secure the shell 3 to the patient's head. The sealed shell 3 then stays still relative to the patient's face even as the patient moves his or her head from side-to-side. The present invention as discussed above will also compensate for any unequally applied forces by side straps 13R and 13L if the patient, for example, were to roll over and his or her pillow were to press laterally against one of the side straps 13R and 13L. Further, although the detent-channel 43, 49 at the top of the shell 3 at the third location C is preferably dimensioned to snap together to hold or maintain the rigid plate 9 on the rigid shell 3, this detent-channel 43, 49 is still preferably a loose fit. That is, the detent 43 and aperture 53 of rigid plate 9 are dimensioned so the detent 43 must be slightly stressed to ride up and over the front wall 55 of channel 49 but once in the channel 49, it is preferably a loose fit. Consequently, if unequal forces develop vertically (e.g., if the patient were to move his or her head to look upward), the present invention can compensate for this by allowing or permitting the rigid plate 9 to rotate about the horizontal axis 73 through locations A and B in FIG. 2. Additionally, the detent-channel arrangements 39/45, 41/47, and 43/49 are loose fitting not only in the forward-rearward directions but also about the axis 75 in FIG. 3. This axis 75 is roughly centered or equal distance from locations A, B, and C and essentially perpendicular to the substantially coplanar axes 63, 65, and 73 and the common plane substantially containing the three locations A, B, and C.

Another feature of the facial mask assembly 1 of the present invention is the swivel hose coupling 10 of FIGS. 8 and 9 connecting the rigid shell 3 to the flexible hose 12. More specifically, the coupling 10 has first and second sections 14 and 16 of hard or rigid plastic. The first rigid section 14 as best seen in FIG. 8 is mounted to the rigid shell 3 for rotation about the first axis 18. The flexible hose 12 (which can be connected to a respiratory device such as a ventilator or continuous positive airway pressure (CPAP) device) is then slid over the rigid tube 20. The tube 20 with the end of hose 12 press fit over it is mounted to the second rigid section 16 so the hose 12 and tube 20 can rotate relative to section 16 about a second axis 22. Additionally, the two rigid sections 14 and 16 are mounted to each other for rotation about a third axis 24. In the extreme positions of FIGS. 8 and 9, the rigid sections 14 and 16 are shown at a right angle to each other with the axes 18 and 22 substantially perpendicular (FIG. 8) and with the axes 18 and 22 substantially parallel (FIG. 9). In these positions and in all positions in between, the axis 24 intersects each of the axes 18 and 22 at a substantially fixed angle 26 of substantially 45 degrees. In this manner and in response to movement of the patient 6 or hose 12 relative to each other, the swivel hose coupling 10 will respond to the creation of any forces between them and allow or permit the rigid shell 3 and flexible hose 12 to rotate relative to each other about axes 18, 22, and/or 24. As discussed above, the loosely mounted rigid plate 9 decouples or isolates the sealing function of the shell 3 and its seal 5 from the attaching function of the harness straps which secure the shell 3 to the patient's head. Similarly, the multiple axis rotation about axes 18, 22, and 24 decouples or isolates the sealing function of shell 3 from the hose attaching function of the coupling 10. Taken together, the modified hose coupling 10 and loosely mounted rigid plate 9 can accommodate a wide variety of motions and forces while maintaining the sealed shell 3 stationary on the patient's face. The patient, hose, and respiratory device can then move or be moved almost at will without breaking the seal of the mask.

While several embodiments of the present invention have been shown and described in detail, it is to be understood that various changes and modifications could be made without departing from the scope of the invention.

We claim:

1. A facial mask assembly for covering at least the nose and nares of a patient's face, said facial mask including:

a rigid, cup-shaped shell dimensioned to substantially surround and enclose at least the nose and nares of the patient's face, means for sealing the shell against the patient's face substantially about at least the nose and nares of the patient in a sealing position substantially centered on the patient's face, and means for attaching the shell to the patient's head with said shell sealed against the patient's face in said sealing position substantially centered on the patient's face, said attaching means including a rigid plate having first and second side portions, means for mounting said rigid plate to said rigid shell with the first side portion of the rigid plate on one side of the patient's nose and the second side portion of the rigid plate on the other side of the patient's nose, and harness means extending substantially about the back of the patient's head and having at least first and second flexible side straps, said first side strap being attached to the rigid plate adjacent the first side portion thereof and said second side strap being attached to the rigid plate adjacent the second side thereof, and means for permitting said rigid plate to move relative to said rigid shell in response to said side straps of said harness means applying unequal forces to the respective side portions of said rigid plate.

2. The facial mask assembly of claim 1 wherein said means for permitting the rigid plate to move relative to said rigid shell in response to the side straps of the harness means applying unequal forces to the respective side portions of said rigid plate includes means for allowing said rigid plate to rotate substantially about a first axis relative to said rigid shell when the force applied by said first strap to the first side portion of said rigid plate is greater than the force applied by the second strap to the second side portion of said rigid plate.

3. The facial mask assembly of claim 2 further including means for allowing said rigid plate to rotate substantially about a second axis relative to said rigid shell when the force applied by the second strap to the second side portion of said rigid plate is greater than the force applied by the first strap to the first side portion of said rigid plate.

4. The facial mask assembly of claim 1 wherein said means for permitting the rigid plate to move relative to said rigid shell in response to the side straps of the harness means applying unequal forces to the respective sides portions of said rigid plate includes means for allowing said rigid plate to selectively rotate substantially about first and second axes to substantially equalize the forces applied by the side straps to the respective side portions of said rigid plate.

5. The facial mask assembly of claim 1 wherein said rigid plate has a top portion and said mounting means for the rigid plate mounts the first side portion thereof to said rigid shell at a first location and mounts the second side portion thereof to said rigid shell at a second location and mounts the top portion thereof to said rigid shell at a third location.

6. The facial mask assembly of claim 5 further including means for allowing said rigid plate to rotate relative to said rigid shell substantially about a first axis extending substantially through said first and third locations when the force applied by the first strap to the first side portion of said rigid plate is greater than the force applied by the second strap to the second side portion of the rigid plate.

7. The facial mask assembly of claim 6 further including means for allowing said rigid plate to rotate relative to said rigid shell substantially about a second axis extending substantially through said second and third locations when the force applied by the second strap to the second side portion of the rigid plate is greater than the force applied by the first strap to the first side portion of the rigid plate.

8. The facial mask assembly of claim 7 further including means for allowing said rigid plate to rotate relative to said rigid shell substantially about a third axis extending substantially through said first and second locations.

9. The facial mask assembly of claim 5 wherein said harness means further includes a third, flexible strap means attached to the rigid plate adjacent the top portion thereof.

10. A facial mask assembly for covering at least the nose and nares of a patient's face, said facial mask assembly including:
a rigid, cup-shaped shell having a rear perimeter portion dimensioned to substantially surround at least the nose and nares of the patient, and sealing means attached substantially about the rear perimeter portion of said rigid shell to engage and seal against the patient's face to enclose at least the nose and nares of the patient within said cup-shaped shell, and
means for securing said cup-shaped shell in a sealing position substantially enclosing at least the nose and nares of the patient within said shell with the sealing means engaging and sealing against the patient's face, said securing means including a substantially rigid plate and means for mounting said rigid plate to said rigid shell at at least three locations, said mounting means including means for allowing said rigid plate to selectively rotate relative to said rigid shell about a first axis extending substantially through said first and third locations and substantially about a second axis extending substantially through said second and third locations.

11. The facial mask assembly of claim 10 wherein said rigid plate has first and second side portions and said rigid shell has first and second side portions and said mounting means mounts said first side portion of said rigid plate to the first side portion of said rigid shell at said first location and mounts the second side portion of said rigid plate to the second side portion of said rigid shell at said second location.

12. The facial mask assembly of claim 11 wherein said rigid shell has a top ridge portion extending substantially along and over the ridge of the patient's nose when said shell is secured in said sealing position and said mounting means mounts said rigid plate to said rigid shell with said third location substantially adjacent the top ridge portion of said rigid shell.

13. The facial mask assembly of claim 12 wherein said rigid plate has an aperture therethrough substantially between said side portions of said rigid plate, said aperture being dimensioned to receive part of the top ridge portion of said rigid shell therein.

14. The facial mask assembly of claim 13 wherein said rigid plate is substantially planar.

15. The facial mask assembly of claim 13 wherein one of said first side portion of said rigid plate and said first side portion of said rigid shell has a first detent extending therefrom and the other of said first side portion of said rigid plate and said first side of said rigid shell has a first channel to receive the first detent.

16. The facial mask assembly of claim 15 wherein said first channel has a closed end and said first detent abuts said closed end when said rigid plate rotates about said first axis.

17. The facial mask assembly of claim 16 wherein one of said second side portion of said rigid plate and said second side portion of said rigid shell has a second detent extending therefrom and the other of said second side portion of said rigid plate and said second side of said rigid shell has a second channel to receive the second detent.

18. The facial mask assembly of claim 17 wherein said second channel has a closed end and said second detent is spaced from said closed end when said rigid plate rotates about said first axis.

19. The facial mask assembly of claim 18 wherein said second channel has an open end spaced from the closed end thereof and said second detent moves toward said open end when said rigid plate rotates about said first axis.

20. The facial mask assembly of claim 19 wherein one of said top portion of said rigid plate and the top ridge portion of said rigid shell has a third detent extending therefrom and the other of said top portion of said rigid plate and the top ridge portion of said rigid shell has a third channel to receive the third detent.

21. The facial mask assembly of claim 20 wherein said third channel has a closed end and said third detent abuts said closed end when said rigid plate rotates about said first axis.

22. The facial mask assembly of claim 20 wherein said third channel includes means for maintaining said third detent therein.

23. The facial mask assembly of claim 20 wherein said first, second, and third channels are in said rigid shell and said first, second, and third detents extend inwardly from said rigid plate into said aperture.

24. The facial mask assembly of claim 10 further including means for allowing said rigid plate to rotate relative to said rigid shell substantially about a third axis.

25. The facial mask assembly of claim 24 wherein said third axis extends substantially through said first and second locations.

26. The facial mask assembly of claim 24 further including means for allowing said rigid plate to rotate relative to said rigid shell about a fourth axis, said fourth axis being substantially perpendicular to a plane substantially containing said first, second, and third locations.

27. The facial mask assembly of claim 24 wherein said third axis is substantially perpendicular to a plane substantially containing said first, second, and third locations.

28. The facial mask assembly of claim 10 wherein said rigid plate has first and second side portions and a top portion and said securing means further includes harness means extending substantially about the rear of the patient's head and having at least first and second, flexible side straps respectively attached adjacent the first and second side portions of said rigid plate, said harness means further having a third, flexible strap means attached adjacent the top portion of said rigid plate.

29. The facial mask assembly of claim 10 further including a swivel hose coupling, said coupling having first and second, rigid sections and means for connecting said first rigid section to said rigid shell for rotation relative to said rigid shell about a first rotational axis and means for connecting said second rigid section to a flexible hose for rotation relative to said hose about a second rotational axis, said coupling further includes means for mounting said first and second rigid sections for rotation relative to each other about a third rotational axis.

30. The facial mask assembly of claim 29 wherein said first and third axes are substantially fixed relative to each other.

31. The facial mask assembly of claim 30 wherein said second and third axes are substantially fixed relative to each other.

32. The facial mask assembly of claim 31 wherein said third rotational axis substantially intersects each of said first and second rotational axes at a substantially 45 degree angle.

33. A facial mask assembly having a rigid shell, a flexible hose, and a swivel hose coupling for connecting said rigid shell to said flexible hose, said coupling having first and second, rigid sections and means for attaching said first rigid section to said rigid shell for rotation relative to said rigid shell about a first rotational axis and means for attaching said second rigid section to said flexible hose for rotation relative to said flexible hose about a second rotational axis, said coupling further including means for mounting said first and second rigid sections for rotation relative to each other about a third rotational axis.

34. The facial mask assembly of claim 33 wherein said first and third rotational axes are substantially fixed relative to each other.

35. The facial mask assembly of claim 34 wherein said second and third rotational axes are substantially fixed relative to each other.

36. The facial mask assembly of claim 35 wherein said third rotational axis substantially intersects each of said first and second rotational axes at substantially a 45 degree angle.

* * * * *

UNITED STATES PATENT AND TRADEMARK OFFICE
CERTIFICATE OF CORRECTION

PATENT NO : 5,662,101  
DATED : September 2, 1997  
INVENTOR(S): Douglas R. Ogden, Joseph A. Abeyta, and Gregg D. Keefe Page 1 of 4

It is certified that error appears in the above-identified patent and that said Letters Patent is hereby corrected as shown below:

Claim 1 at line 12 of column 6, delete "the" and substitute -- a patient's --.

Claim 1 at line 13 of column 6, delete "of a patient's face".

Claim 1 at line 13 of column 6, insert -- assembly -- after "mask".

Claim 1 at line 15 of column 6, delete the first recitation of "the" and substitute -- a patient's --.

Claim 1 at line 15 of column 6, delete "of the".

Claim 1 at line 16 of column 6, delete "patient's face".

Claim 1 at line 16 of column 6, delete the first recitation of "the" and substitute -- a --.

Claim 1 at line 17 of column 6, delete "the" and substitute -- a patient's --.

Claim 1 at line 18 of column 6, delete "of the patient".

Claim 1 at line 19 of column 6, delete "the" and substitute -- a --.

Claim 1 at line 20 of column 6, delete "the" and substitute -- a --.

UNITED STATES PATENT AND TRADEMARK OFFICE
CERTIFICATE OF CORRECTION

PATENT NO : 5,662,101

DATED : September 2, 1997

INVENTOR(S): Douglas R. Ogden, Joseph A. Abeyta, and Gregg D. Keefe

It is certified that error appears in the above-identified patent and that said Letters Patent is hereby corrected as shown below:

Claim 1 at line 21 of column 6, delete "the" and substitute -- a --.

Claim 1 at line 22 of column 6, delete "the" and substitute -- a --.

Claim 1 at line 26 of column 6, delete the second recitation of "the" and substitute -- a --.

Claim 1 at line 28 of column 6, delete "the" and substitute -- a --.

Claim 1 at line 29 of column 6, delete "the" and substitute -- a --.

Claim 10 at line 20 of column 7, delete "the" and substitute -- a patient's --.

Claim 10 at line 21 of column 7, delete "of a patient's face".

Claim 10 at line 24 of column 7, delete "the" and substitute -- a patient's --.

Claim 10 at line 25 of column 7, delete "of the patient".

Claim 10 at line 27 of column 7, delete "the" and substitute -- a --.

UNITED STATES PATENT AND TRADEMARK OFFICE
CERTIFICATE OF CORRECTION

PATENT NO : 5,662,101
DATED : September 2, 1997
INVENTOR(S): Douglas R. Ogden, Joseph A. Abeyta, and Gregg D. Keefe It is certified that error appears in the above-identified patent and that said Letters Patent is hereby corrected as shown below:

Claim 10 at line 28 of column 7, delete the first recitation of "the" and substitute -- a patient's --.

Claim 10 at line 28 of column 7, delete "of the patient".

Claim 10 at line 31 of column 7, delete "the" and substitute -- a patient's --.

Claim 10 at line 32 of column 7, delete "of the patient".

Claim 10 at line 33 of column 7, delete "the" and substitute -- a --.

Claim 12 at line 53 of column 7, delete the second recitation of "the" and substitute -- a --.

Claim 28 at line 55 of column 8, delete the second recitation of "the" and substitute -- a --.

Claim 32 at line 10 of column 9, delete "32" and substitute -- 31 --.

Claim 33 at line 15 of column 9, after "hose," but before "said", insert -- a rigid, cup-shaped shell dimensioned to substantially surround and enclose at least a patient's nose and nares, means for sealing the shell against a

UNITED STATES PATENT AND TRADEMARK OFFICE
CERTIFICATE OF CORRECTION

PATENT NO : 5,662,101
DATED : September 2, 1997
INVENTOR(S): Douglas R. Ogden, Joseph A. Abeyta, and Gregg D. Keefe It is certified that error appears in the above-identified patent and that said Letters Patent is hereby corrected as shown below:

patient's face substantially about at least a patient's nose and nares in a sealing position substantially centered on a patient's face, and means for attaching the shell to a patient's head with said shell sealed against a patient's face in sealing position substantially centered on a patient's face, --.

Signed and Sealed this

Tenth Day of August, 1999

Q. TODD DICKINSON

Attest:

Attesting Officer

Acting Commissioner of Patents and Trademarks